(12) United States Patent
Kibby et al.

(10) Patent No.: US 7,943,674 B1
(45) Date of Patent: May 17, 2011

(54) ZEOLITE SUPPORTED COBALT HYBRID FISCHER-TROPSCH CATALYST

(75) Inventors: Charles L. Kibby, Benicia, CA (US); Kandaswamy Jothimurugesan, Hercules, CA (US); Tapan K. Das, Albany, CA (US); Robert J. Saxton, Pleasanton, CA (US); Allen W. Burton, Jr., Stewartsville, NJ (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 12/622,972

(22) Filed: Nov. 20, 2009

(51) Int. Cl.
*C07C 27/00* (2006.01)
(52) U.S. Cl. .......................... 518/715; 518/700
(58) Field of Classification Search .................. 518/700, 518/715
See application file for complete search history.

(56) References Cited

U.S. PATENT DOCUMENTS

| | | | |
|---|---|---|---|
| 4,294,725 A | 10/1981 | Franenkel et al. |
| 4,492,774 A | 1/1985 | Kibby et al. |
| 4,556,645 A | 12/1985 | Coughlin et al. |
| 4,585,798 A | 4/1986 | Beuther et al. |
| 4,605,679 A | 8/1986 | Kobylinski et al. |
| 4,617,283 A | 10/1986 | Coughlin |
| 4,617,320 A | 10/1986 | Coughlin et al. |
| 4,622,308 A | 11/1986 | Koikeda et al. |
| 4,632,941 A | 12/1986 | Coughlin |
| 4,652,538 A | 3/1987 | Rabo et al. |
| 4,663,355 A | 5/1987 | Coughlin |
| 4,670,414 A | 6/1987 | Kobylinski et al. |
| 4,822,824 A | 4/1989 | Iglesia et al. |
| 4,874,733 A | 10/1989 | Miller et al. |
| 4,906,671 A | 3/1990 | Haag et al. |
| 5,036,032 A | 7/1991 | Iglesia et al. |
| 5,104,902 A | 4/1992 | Bessell |
| 5,126,377 A | 6/1992 | Bessell |
| 5,128,377 A | 7/1992 | Behrmann et al. |
| 5,140,050 A | 8/1992 | Mauldin et al. |
| 5,168,091 A | 12/1992 | Behrmann et al. |
| 5,292,705 A | 3/1994 | Mitchell |
| 5,424,264 A | 6/1995 | Richard et al. |
| 5,545,674 A | 8/1996 | Behrmann et al. |
| 5,728,918 A | 3/1998 | Nay et al. |
| 5,733,839 A | 3/1998 | Espinoza et al. |
| 6,191,066 B1 | 2/2001 | Singleton et al. |
| 6,245,709 B1 | 6/2001 | Clark et al. |
| 6,262,131 B1 | 7/2001 | Arcuri et al. |
| 6,313,062 B1 | 11/2001 | Krylova et al. |
| 6,331,574 B1 | 12/2001 | Lapidus et al. |
| 6,331,575 B1 | 12/2001 | Mauldin |
| 6,465,529 B1 | 10/2002 | Oaage et al. |
| 6,472,441 B1 | 10/2002 | Kibby |
| 6,491,880 B1 | 12/2002 | Want et al. |
| 6,521,565 B1 | 2/2003 | Clavenna et al. |
| 6,531,517 B1 | 3/2003 | Wachter et al. |
| 6,602,921 B2 | 8/2003 | Manzer et al. |
| 6,638,889 B1 | 10/2003 | Van Berge et al. |
| 6,649,662 B2 | 11/2003 | Kibby |
| 6,706,661 B1 | 3/2004 | Krylova et al. |
| 6,753,351 B2 | 6/2004 | Clark et al. |
| 7,045,486 B2 | 5/2006 | Wang et al. |
| 7,157,501 B2 | 1/2007 | Steenwinkel et al. |
| 7,300,959 B2 | 11/2007 | Vogt et al. |
| 7,361,619 B2 | 4/2008 | Malek et al. |
| 7,384,986 B2 | 6/2008 | Huang et al. |
| 2010/0160464 A1 | 6/2010 | Kirby et al. |

FOREIGN PATENT DOCUMENTS

| | | |
|---|---|---|
| EP | 153517 | 9/1985 |
| EP | 04105668 | 5/2006 |
| RU | 2295387 * | 3/2007 |
| WO | 99/61550 A1 | 12/1999 |
| WO | 03/002252 A1 | 1/2003 |
| ZA | 855317 | 7/1985 |

OTHER PUBLICATIONS

Martinez, et al., The Application of Zeolites and Periodic Mesoporous Silicas in the Catalytic Conversion of Synthesis Gas, Dec. 23, 2008, Springer Science+Business Media.

Li, et al., Gasoline-range hydrocarbon synthesis over Co/Si02IHZSM-5 catalyst with C02-containing syngas, 91, Fuel Processing Technology, 1991.

Yang, et al., Sesign and Modification of Zeolite Capsule Catalyst, A Confined Reaction Field, and its Application in One-Sep Isoparaffin Synthesis from Syngas, 2008, Energy & Fuels.

Martinez, et al., Catalytic behavior of hybrid Co/SI02-(medium-pore) zeolite catalysts during the one-stage conversion of syngas to gasoline, 2008, Applied Catalysis.

Zola, et al., Cobalt Supported on Different Zeolites for Fischer=Tropsch Synthesis, 2007, Elsevier B.V.

Thongkam, et al., Novel Three-component Zeolite Capsule Catalyst for Direct Synthesis of Isoparaffin, 2009, Journal of the Japan Petroleum Institute.

* cited by examiner

*Primary Examiner* — Jafar Parsa
(74) *Attorney, Agent, or Firm* — Karen R. DiDomenicis; Richard Schulte

(57) ABSTRACT

A method for performing synthesis gas conversion is disclosed which comprises contacting synthesis gas with a hybrid Fischer-Tropsch catalyst formed by impregnating a ZSM-12 zeolite extrudate using a solution, for example, a substantially non-aqueous solution, comprising a cobalt salt and activating the impregnated zeolite extrudate by a reduction-oxidation-reduction cycle. The method results in reduced methane yield and increased yield of liquid hydrocarbons substantially free of solid wax.

6 Claims, No Drawings

ZEOLITE SUPPORTED COBALT HYBRID FISCHER-TROPSCH CATALYST

FIELD

The present disclosure relates to a process for the conversion of synthesis gas to liquid hydrocarbons in the presence of a zeolite supported cobalt catalyst.

BACKGROUND

High quality fuels remain in increasing demand with respect to the crude oil crisis and environmental impact. Fischer-Tropsch synthesis, which involves the production of hydrocarbons by the catalyzed reaction of CO and hydrogen, can convert natural gas derived synthesis gas to liquid fuels and high-value chemicals. Fischer-Tropsch synthesis is one of the more attractive direct and environmentally acceptable paths to high quality transportation fuels.

Fischer-Tropsch catalysts are typically based on group VIII metals such as, for example, Fe, Co, Ni and Ru, with Fe and Co being the most popular. The product distribution over such catalysts is non-selective and is generally governed by the Anderson-Schulz-Flory (ASF) polymerization kinetics.

What is needed is a process for the conversion of synthesis gas to liquid hydrocarbons utilizing a Fischer-Tropsch catalyst comprising cobalt, with its low water gas shift activity and ready availability, that produces reduced methane and results in a liquid hydrocarbon product substantially free of solid wax with a lower yield of methane and a higher yield of $C_{11}^+$ hydrocarbon product as compared with known conversion processes.

SUMMARY

The invention relates to a method of performing a synthesis gas conversion reaction, the method comprising contacting a hybrid Fischer-Tropsch catalyst comprising a ZSM-12 zeolite extrudate impregnated with cobalt with synthesis gas, the synthesis gas comprising hydrogen and carbon monoxide at a ratio of hydrogen to carbon monoxide of between about 1 and about 3, at a temperature of between about 180 and about 280° C., at a pressure of about 5 and about 30 atmospheres to yield a product containing:
  less than about 10 weight % methane;
  greater than about 75 weight % $C_{5+}$;
  less than about 15 weight % $C_2$-$C_4$; and
  less than about 5 weight % $C_{21+}$;
  wherein the product is substantially free of solid wax.

DETAILED DESCRIPTION

Impregnation methods followed by reduction-oxidation-reduction activation are employed for making a practical hybrid Fischer-Tropsch catalyst. Cobalt-ruthenium/zeolite catalysts with high activities for synthesis gas conversion to hydrocarbon liquids have been prepared using commercially available, alumina bound zeolite extrudates. With cobalt nitrate, metal loading in a single step impregnation is limited from 1 to 10 weight % cobalt for these alumina bound zeolites. Thus, multiple impregnations are often needed, with intervening drying and calcination treatments to disperse and decompose the metal salts. The cobalt content can be varied from 5 weight % to 15 weight %. Usually, calcination in air produces materials with lower activities than those formed by direct reduction of cobalt nitrate. However, direct reduction on a large scale is considered to be undesirable since it is very exothermic and it produces a pyrophoric catalyst that must then be passivated before it can be handled in air. A low temperature reduction-oxidation-reduction cycle has been found superior to a single reduction step for the activation of cobalt-ruthenium/zeolite catalysts for synthesis gas conversion. Such a method for preparing and activating catalysts for synthesis gas conversion is disclosed in co-pending U.S. patent application Ser. No. 12/343,534.

As disclosed in co-pending U.S. patent application Ser. No. 12/343,534, the use of zeolite extrudates has been found to be beneficial, for the relatively larger zeolite extrudate particles will cause less pressure drop within a reactor and be subject to less attrition than zeolite powder or even granular zeolite (e.g., having a particle size of about 300-1000 microns). Formation of particles from zeolite powder or granular zeolite plus Co/alumina and a binder, to be sized equivalent to zeolite extrudate (i.e., to avoid pressure drop and attrition) would result in blinding of cobalt sites and would probably still result in some ion exchange during the required drying and calcination steps, thus lowering the activity and selectivity of the resultant catalyst.

Methods of formation of zeolite extrudates are readily known to those of ordinary skill in the art. Wide variations in macroporosity are possible with such extrudates. For the present application, without wishing to be bound by any theories, it is believed that as high a macroporosity as possible, consistent with high enough crush strength to enable operation in long reactor tubes, will be advantageous in minimizing diffusion constraints on activity and selectivity. The zeolite-mediated Fischer-Tropsch synthesis is not as diffusion-limited as that of normal Fischer-Tropsch synthesis, since the pores of the presently disclosed zeolite supported Fischer-Tropsch catalyst stay open during operation, whereas the pores of a normal Fischer-Tropsch catalyst fill with oil (melted wax).

In extrudate formation, strength is produced in a calcination step at high temperature. The temperature is high enough to cause solid state reactions between cobalt oxides and alumina or aluminosilicate portions of the material, to form very stable, essentially non-reducible phases such as spinels. Consequently, it is desirable that the metal be added after the extrudate has been formed and has already undergone calcination.

As used herein, the phrase "hybrid Fischer-Tropsch catalyst" refers to a Fischer-Tropsch catalyst comprising a Fischer-Tropsch base component as well as a component containing the appropriate functionality to convert in a single-stage the primary Fischer-Tropsch products into desired products (i.e., minimize the amount of heavier, undesirable products, i.e. $C_{21+}$). Thus, the combination of a Fischer-Tropsch component displaying high selectivity to short-chain α-olefins and oxygenates with zeolite(s) results in an enhanced gasoline selectivity and an increased concentration of high-octane branched and aromatic hydrocarbons by promoting oligomerization, cracking, isomerization, and aromatization reactions on the zeolite acid sites. Gasoline-range isoparaffins also can be produced in a single reactor using hybrid catalysts by combining a cobalt-based Fischer-Tropsch component with an acidic or bifunctional zeolite component. Primary waxy products formed on the cobalt component are cracked/hydrocracked (i.e., by the acidic zeolite component) into mainly branched hydrocarbons with limited formation of aromatics, a less desirable component in reformulated gasolines due to environmental concerns. In particular, in a single-stage Fischer-Tropsch reaction, the presently disclosed hybrid Fischer-Tropsch catalyst provides:

less than about 10 weight %, even between about 3 and about 10 weight % $CH_4$;

less than about 15 weight %, even between about 3 and about 10 weight % $C_2$-$C_4$;

greater than about 75 weight % $C_{5+}$; and less than about 5 weight % $C_{21+}$;

wherein a liquid product is formed that is substantially free of solid wax, by which is meant that there is no insoluble solid wax phase at ambient conditions, i.e. 20° C. at 1 atmosphere. As a result, there is no need to separately treat a wax phase. By wax is meant $C_{21+}$ paraffins.

As used herein, the phrase "zeolite supported cobalt catalyst" refers to catalyst wherein the cobalt metal is distributed as small crystallites upon the zeolite support. The cobalt content of the zeolite supported cobalt catalyst can depend on the alumina content of the zeolite. For example, for an alumina content of about 20 weight % to about 99 weight % based upon support weight, the catalyst can contain, for example, from about 1 to about 20 weight % cobalt, preferably 5 to about 15 weight % cobalt, based on total catalyst weight, at the lowest alumina content. At the highest alumina content the catalyst can contain, for example, from about 5 to about 30 weight % cobalt, preferably from about 10 to about 25 weight % cobalt, based on total catalyst weight.

It has been found that synthesis gas comprising hydrogen and carbon monoxide can be selectively converted under synthesis gas conversion conditions to liquid hydrocarbons with a catalyst prepared by subjecting a zeolite supported cobalt catalyst to an activation procedure comprising the steps, in sequence, of (A) reduction in hydrogen, (B) oxidation in an oxygen-containing gas, and (C) reduction in hydrogen, the activation procedure being conducted at a temperature below 500° C. It has been found that the activation procedure of the present disclosure provides zeolite supported cobalt catalyst with improved reaction rates when the catalyst is prepared by impregnation of a zeolite support with cobalt. Moreover, the activation procedure of the present disclosure can significantly improve activity of promoted, zeolite supported cobalt catalyst, wherein a promoter such as, for example, Ru, Rh, Pd, Cu, Ag, Au, Zn, Cd, Hg, and/or Re has been previously added to improve activity. The catalyst of the present disclosure is produced by subjecting a zeolite supported cobalt catalyst to an activation procedure including the steps of (i) reduction, (ii) oxidation, and (iii) reduction, herein termed "ROR activation" while under a temperature below 500° C., for example, below 450° C. By subjecting the zeolite supported cobalt catalyst to ROR activation, the activity of the resultant catalyst can be increased by as much as about 100% using the activation procedure of the present disclosure.

Zeolites are one subset of the larger group of molecular sieves. A zeolite is a crystalline, microporous aluminosilicate that contains silica and aluminum in the tetrahedral framework positions. Acid sites are generated from the charge imbalance between +3 aluminum and +4 silica sites. Other metal oxides may be substituted in place of or in addition to aluminum. Molecular sieves of this more general type include, but are not limited to, silica-only (silicates), borosilicates, germanosilicates, titanosilicates, gallosilicates and mixtures thereof.

Molecular sieves, in turn, are crystalline materials that have regular passages (pores). If examined over several unit cells of the structure, the pores will form an axis based on the same units in the repeating crystalline structure. While the overall path of the pore will be aligned with the pore axis, within a unit cell, the pore may diverge from the axis, and it may expand in size (to form cages) or narrow. The axis of the pore is frequently parallel with one of the axes of the crystal. The narrowest position along a pore is the pore mouth. The pore size refers to the size of the pore mouth. The pore size is calculated by counting the number of tetrahedral positions that form the perimeter of the pore mouth. A pore that has 10 tetrahedral positions in its pore mouth is commonly called a 10-ring pore. Pores of relevance to catalysis in this application have pore sizes of 8 rings or greater. If a molecular sieve has only one type of relevant pore with an axis in the same orientation to the crystal structure, it is called 1-dimensional. Molecular sieves may have pores of different structures or may have pores with the same structure but oriented in more than one axis related to the crystal. In these cases, the dimensionality of the molecular sieve is determined by summing the number of relevant pores with the same structure but different axes with the number of relevant pores of different shape.

A zeolite extrudate impregnated with cobalt using a ZSM-12-type zeolite (IZA Structure Code MTW) has been found to be a particularly effective catalyst for use in a Fischer-Tropsch type reaction where low methane yield is desired and a liquid hydrocarbons product substantially free of solid wax is desired.

The structure of ZSM-12 contains a single-dimension channel system in which the opening is a 12-member ring 5.7×6.1 A in size. The absence of channel intersections or pockets as would be found in a multi-dimensional channel system of, for example, ZSM-5 or Beta zeolite, has been found to provide unique reactivity in the isomerization and cracking of α-olefins that are formed from the Fischer-Tropsch base component. By optimizing the acidic functionality of the ZSM-12 zeolite it has been found that the hybrid Fischer-Tropsch catalyst of the present invention gives a liquid hydrocarbon product substantially free of solid wax with a low yield of methane and a high yield of $C_{11+}$ hydrocarbon product.

The ZSM-12 zeolite supports can have an external surface area of between about 100 $m^2/g$ and about 300 $m^2/g$, for example, about 180 $m^2/g$. Micropore value for 80% ZSM-12 should be between about 90 and 112 μL/g, with lower values implying some occlusion or loss of micropore structure. BET surface area is a sum of external area and micropore area (more properly calculated as a volume). The zeolite supports can further have porosities of between about 30 and 80%, total intrusion volumes between about 0.25 and 0.60 cc/g, and crush strengths between about 1.25 and 5 lb/mm The ratio of silica to aluminum in the ZSM-12 zeolite component can be between about 10 and 100.

A promoter, such as ruthenium or the like may be included in the catalyst of the present disclosure if desired. For a catalyst containing about 10 weight % cobalt, the amount of ruthenium can be from about 0.01 to about 0.50 weight %, for example, from about 0.05 to about 0.25 weight % based upon total catalyst weight. The amount of ruthenium would accordingly be proportionately higher or lower for higher or lower cobalt levels, respectively. A cobalt level of about 7.5 weight % has been found to be best for 80 weight % ZSM-12 and 20 weight % alumina.

The ROR activation procedure of the present disclosure may be used to improve activity of the zeolite supported catalyst of the present disclosure. Thus, any technique well known to those having ordinary skill in the art to distend the catalytic metals in a uniform manner on the catalyst zeolite support is suitable, assuming they do not promote ion exchange with zeolite acid sites.

The method employed to deposit the catalytic metals of the present disclosure onto the zeolite support can involve an impregnation technique using a substantially non-aqueous solution containing soluble cobalt salt and, if desired, a soluble promoter metal salt, e.g., ruthenium salt, in order to achieve the necessary metal loading and distribution required to provide a highly selective and active catalyst.

Initially, the zeolite support can be treated by oxidative calcination at a temperature in the range of from about 450° to about 900° C., for example, from about 600° to about 750° C. to remove water and any organics from the zeolite support.

Meanwhile, non-aqueous organic solvent solution of a cobalt salt, and, if desired, aqueous or non-aqueous organic solvent solutions of ruthenium salts, for example, are prepared. Any suitable ruthenium salt, such as ruthenium nitrate, chloride, acetate or the like can be used. Solutions for the promoters can contain water in small amounts. As used herein, the phrase "substantially non-aqueous" refers to a solution that includes at least 95 volume % of a non-aqueous component. In general, any metal salt which is soluble in the organic solvent of the present disclosure and will not have a poisonous effect on the catalyst can be utilized.

The non-aqueous organic solvent is a non-acidic liquid which is formed from moieties selected from the group consisting of carbon, oxygen, hydrogen and nitrogen, and possesses a relative volatility of at least 0.1. The phrase "relative volatility" refers to the ratio of the vapor pressure of the solvent to the vapor pressure of acetone, as reference, when measured at 25° C.

It has been found that an aqueous solution containing a cobalt salt migrates into the microporous hydrophilic zeolite, and cobalt cations replace protons at zeolite acid sites. In contrast, use of a non-aqueous solution containing a cobalt salt minimizes replacement of zeolite acid sites with metal. In particular, when cobalt ions in solution exchange with acidic protons in the zeolite, the cobalt ions essentially titrate the acidic sites, since the ability of the cobalt ion to promote acid-catalyzed reactions is much less than that of the protons they displace. This would not matter if the cobalt in those positions was easy to reduce during catalyst activation, because reduction by hydrogen during that process would regenerate the proton acidity according to the equation: $Co^{+2}+H_2=Co^0+2H^+$. Unfortunately, the ion exchange sites are quite stable positions for cobalt and cobalt ions there are not readily reduced during normal activation procedures. As the reduction in the amount of reducible Co also decreases the activity of the Fischer-Tropsch component in the catalyst, it is undesirable for both functions.

Suitable solvents include, for example, ketones, such as acetone, butanone (methyl ethyl ketone); the lower alcohols, e.g., methanol, ethanol, propanol and the like; amides, such as dimethyl formamide; ethers, such as diethylether and tetrahydrofuran; hydrocarbons, such as pentane and hexane; and mixtures of the foregoing solvents. In an embodiment, the solvents are acetone, for cobalt nitrate or tetrahydrofuran.

Suitable cobalt salts include, for example, cobalt nitrate, cobalt acetate, cobalt carbonyl, cobalt acetylacetonate, or the like. Likewise, any suitable ruthenium salt, such as ruthenium nitrate, chloride, acetate or the like can be used. In an embodiment, ruthenium acetylacetonate is used. In general, any metal salt that is soluble in the organic solvent of the present disclosure, or in a solution of that solvent with no more than 5 vol % water, and will not have a poisonous effect on the metal catalyst or on the acid sites of the zeolite can be utilized.

The calcined zeolite support is then impregnated in a dehydrated state with the substantially non-aqueous, organic solvent solution of the metal salts. Thus, the calcined zeolite support should not be unduly exposed to atmospheric humidity so as to become rehydrated.

Any suitable impregnation technique can be employed including techniques well known to those skilled in the art so as to distend the catalytic metals in a uniform thin layer on the catalyst zeolite support. For example, the cobalt along with the oxide promoter can be deposited on the zeolite support material by the "incipient wetness" technique. Such technique is well known and requires that the volume of substantially non-aqueous solution be predetermined so as to provide the minimum volume which will just wet the entire surface of the zeolite support, with no excess liquid. Alternatively, the excess solution technique can be utilized if desired. If the excess solution technique is utilized, then the excess solvent present, e.g., acetone, is merely removed by evaporation.

Next, the substantially non-aqueous solution and zeolite support are stiffed while evaporating the solvent at a temperature of from about 25° to about 50° C. until "dryness."

The impregnated catalyst is slowly dried at a temperature of from about 110° to about 120° C. for a period of about 1 hour so as to spread the metals over the entire zeolite support. The drying step is conducted at a very slow rate in air.

The dried catalyst may be reduced directly in hydrogen or it may be calcined first. In the case of impregnation with cobalt nitrate, direct reduction can yield a higher cobalt metal dispersion and synthesis activity, but reduction of nitrates is difficult to control and calcination before reduction is safer for large scale preparations. Also, a single calcination step to decompose nitrates is simpler if multiple impregnations are needed to provide the desired metal loading. Reduction in hydrogen requires a prior purge with inert gas, a subsequent purge with inert gas and a passivation step in addition to the reduction itself, as described later as part of the ROR activation. However, impregnation of cobalt carbonyl must be carried out in a dry, oxygen-free atmosphere and it must be decomposed directly, then passivated, if the benefits of its lower oxidation state are to be maintained.

The dried catalyst is calcined by heating slowly in flowing air, for example 10 cc/gram/minute, to a temperature in the range of from about 200° to about 350° C., for example, from about 250° to about 300° C., that is sufficient to decompose the metal salts and fix the metals. The aforesaid drying and calcination steps can be done separately or can be combined. However, calcination should be conducted by using a slow heating rate of, for example, 0.5° to about 3° C. per minute or from about 0.5° to about 1° C. per minute and the catalyst should be held at the maximum temperature for a period of about 1 to about 20 hours, for example, for about 2 hours.

The foregoing impregnation steps are repeated with additional substantially non-aqueous solutions in order to obtain the desired metal loading. Ruthenium and other promoter metal oxides are conveniently added together with cobalt, but they may be added in other impregnation steps, separately or in combination, either before, after, or between impregnations of cobalt.

After the last impregnation sequence, the loaded catalyst zeolite support is then subjected to the ROR activation treatment of the present disclosure. The ROR activation treatment of the present disclosure must be conducted at a temperature considerably below 500° C. in order to achieve the desired increase in activity and selectivity of the cobalt-impregnated catalyst. Temperatures of 500° C. or above reduce activity and liquid hydrocarbon selectivity of the cobalt-impregnated catalyst. Suitable ROR activation temperatures are below 500° C., preferably below 450° C. and most preferably, at or below 400° C. Thus, ranges of 100° or 150° to 450° C., for example, 250° to 400° C. are suitable for the reduction steps. The oxidation step should be limited to 200° to 300° C. These activation steps are conducted while heating at a rate of from about 0.1° to about 2° C., for example, from about 0.1° to about 1° C.

The impregnated catalyst can be slowly reduced in the presence of hydrogen. If the catalyst has been calcined after each impregnation, to decompose nitrates or other salts, then the reduction may be performed in one step, after an inert gas purge, with heating in a single temperature ramp (e.g., 1° C./min.) to the maximum temperature and held at that temperature, from about 250° or 300° to about 450° C., for example, from about 350° to about 400° C., for a hold time of 6 to about 65 hours, for example, from about 16 to about 24 hours. Pure hydrogen is preferred in the first reduction step. If nitrates are still present, the reduction is best conducted in two steps wherein the first reduction heating step is carried out at a slow heating rate of no more than about 5° C. per minute, for example, from about 0.1° to about 1° C. per minute up to a maximum hold temperature of 200° to about 300° C., for example, 200° to about 250° C., for a hold time between about 6 to about 24 hours, for example, from about 16 to about 24 hours under ambient pressure conditions. In the second treating step of the first reduction, the catalyst can be heated at from about 0.1° to about 1° C. per minute to a maximum hold temperature between about 250° or 300° up to about 450° C., for example, from about 350° to about 400° C. for a hold time of 6 to about 65 hours, for example, from about 16 to about 24 hours. Although pure hydrogen is preferred for these reduction steps, a mixture of hydrogen and nitrogen can be utilized.

Thus, the reduction may involve the use of a mixture of hydrogen and nitrogen at 100° C. for about one hour; increasing the temperature 0.5° C. per minute until a temperature of 200° C.; holding that temperature for approximately 30 minutes; and then increasing the temperature 1° C. per minute until a temperature of 350° C. is reached and then continuing the reduction for approximately 16 hours. Reduction should be conducted slowly enough and the flow of the reducing gas maintained high enough to maintain the partial pressure of water in the offgas below 1%, so as to avoid excessive steaming of the exit end of the catalyst bed. Before and after all reductions, the catalyst must be purged in an inert gas such as nitrogen, argon or helium.

The reduced catalyst is passivated at ambient temperature (25°-35° C.) by flowing diluted air over the catalyst slowly enough so that a controlled exotherm of no larger than +50° C. passes through the catalyst bed. After passivation, the catalyst is heated slowly in diluted air to a temperature of from about 300° to about 350° C. (preferably 300° C.) in the same manner as previously described in connection with calcination of the catalyst.

The temperature of the exotherm during the oxidation step should be less than 100° C., and will be 50-60° C. if the flow rate and/or the oxygen concentration are dilute enough. If it is even less, the oxygen is so dilute that an excessively long time will be needed to accomplish the oxidation. There is a danger in exceeding 300° C. locally, since cobalt oxides interact with alumina and silica at temperatures above 400° C. to make unreducible spinels, and above 500° C., Ru makes volatile, highly toxic oxides.

Next, the reoxidized catalyst is then slowly reduced again in the presence of hydrogen, in the same manner as previously described in connection with the initial reduction of the impregnated catalyst. This second reduction is much easier than the first. Since nitrates are no longer present, this reduction may be accomplished in a single temperature ramp and hold, as described above for reduction of calcined catalysts.

The composite catalyst of the present disclosure has an average particle diameter, which depends upon the type of reactor to be utilized, of from about 0.01 to about 6 millimeters; for example, from about 1 to about 6 millimeters for a fixed bed; and for example, from about 0.01 to about 0.11 millimeters for a reactor with the catalyst suspended by gas, liquid, or gas-liquid media (e.g., fluidized beds, slurries, or ebullating beds).

The charge stock used in the process of the present disclosure is a mixture of CO and $H_2$ having a ratio of $H_2$ to CO of between about 1 and about 3, even between about 1.5 and about 2. Any suitable source of the CO and $H_2$ can be used. The charge stock can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of the present disclosure, but it may be present as a diluent gas. Sulfur compounds in any form are deleterious to the life of the catalyst and should be removed from the CO—$H_2$ mixture and from any diluent gases.

The reaction temperature is suitably from about 180° to about 280° C., for example, from about 220° to about 235° C. The total pressure is, for example, from about 5 to about 30 atmospheres, for example, from about 20 to about 30 atmospheres.

The gaseous hourly space velocity based upon the total amount of feed is less than 20,000 volumes of gas per volume of catalyst per hour, for example, from about 100 to about 5000 v/v/hour or from about 1000 to about 2500 v/v/hour. If desired, pure synthesis gas can be employed or, alternatively, an inert diluent, such as nitrogen, $CO_2$, methane, steam or the like can be present. The phrase "inert diluent" indicates that the diluent is non-reactive under the reaction conditions or is a normal reaction product.

The synthesis gas reaction using the catalysts of the present disclosure can occur in a fixed, fluid or moving bed type of operation.

The following illustrative examples are intended to be non-limiting.

EXAMPLES

Direct Synthesis of Small Crystal Al-ZSM-12 Using an SDA in Combination with an Ancillary Organic Component 105.6 g of sodium silicate solution (28 wt % $SiO_2$, 8.9 wt % $Na_2O$ available from Fisher Scientific Inc.) was mixed with 104.4 g of deionized water inside a 600-mL Teflon® PTFE liner. Next, in a second step, 38 g of a 75% methyltriethylammonium chloride solution (available from SACHEM, Austin, Tex.) and 2.39 g of 1,6-bis(2,3-dimethylimidazolium)hexane dibromide salt were dissolved in 122.5 g of deionized water, and this solution was mixed with the silicate solution. Then 7.03 g of aluminum nitrate nonahydrate was dissolved in 227.1 g of deionized water. The aluminum nitrate solution was added to the silicate solution with continuous stiffing to form a uniform suspension. Next 6.4 g of sulfuric acid (98%) was added to the suspension and mixed to form a uniform gel. The gel was mixed for an hour. The liner was then sealed within an autoclave (available from Parr Instrument Company). The autoclave was heated under static conditions to 155° C. over a 4-hr period and then allowed to remain at 155° C. for 80 hours. The solid products were recovered from the cooled reactor by vacuum filtration and washed with copious quantities of water. The solids were then allowed to dry in an oven at 95° C. for over 12 hours. The powder X-ray diffraction pattern indicated the product was pure ZSM-12. The Si/Al ratio was determined to be 24.3.

Preparation of Catalyst Comprising 7.5 Weight % Co-0.19 Weight % Ru Supported on 80 Weight % ZSM-12 and 20 Weight % Alumina ZSM-12 powder was first calcined at 550° C. for 2 hours. 50 g of the calcined ZSM-12 powder and 12.5 g of catapal B alumina powder was added to a mixer and mixed for 10 minutes. 30.6 g of deionized water and 0.89 g of nitric acid was added to the mixed powder and mixed for 10 minutes. The mixture was then transferred to a 1 inch BB gun extruder available from The Bonnot Company (Uniontown, Ohio) and extruded through a dieplate containing forty-eight $1/16$" holes. The ZSM-12 extrudates were dried first at 70° C. for 2 hours, then at 120° C. for 2 hours and finally calcined in flowing air at 600° C. for 2 hours.

A catalyst containing 7.5% Co-0.19% Ru on $1/16$" alumina-bound ZSM-12 extrudates was prepared in a single step using non-aqueous impregnation. The ZSM-12 extrudates prepared above were used. First, 0.259 g of ruthenium(III) nitrosyl nitrate (available from Alfa Aesar) was dissolved in 4 g of deionized water. Second, 16.049 g of cobalt(II) nitrate hexahydrate (available from Sigma-Aldrich) was dissolved in 80 g of acetone. The two solutions were then mixed together and added to the 40 g of dry alumina-bound ZSM-12 extrudates. The solvent was removed in a rotary evaporator under vacuum by heating slowly to 45° C. The vacuum-dried material was then further dried in air in an oven at 120° C. overnight. The dried catalyst was then calcined at 300° C. for 2 hours in a muffle furnace.

Properties of the extrudate and catalyst are set forth in Table 1.

TABLE 1

| Catalyst Composition | Micropore Area, m²/g | External Surface Area, m²/g | BET Surface Area, m²/g | Metal Dispersion, % | Average Particle Diameter, nm |
|---|---|---|---|---|---|
| 80% ZSM-12 + 20% Al₂O₃ | 167 | 98 | 264 | na | na |
| 7.5% Co-0.19 Ru/ (80% ZSM-12 + 20% Al₂O₃) | 55 | 61 | 115 | 15.2 | 6.5 |

Activation of Bimetallic Catalysts

Ten grams of catalyst as prepared above was charged to a glass tube reactor. The reactor was placed in a muffle furnace with upward gas flow. The tube was purged first with nitrogen gas at ambient temperature, after which time the gas feed was changed to pure hydrogen with a flow rate of 750 sccm. The temperature to the reactor was increased to 350° C. at a rate of 1° C./minute and then held at that temperature for six hours. After this time, the gas feed was switched to nitrogen to purge the system and the unit was then cooled to ambient temperature. Then a gas mixture of 1 volume % $O_2/N_2$ was passed up through the catalyst bed at 750 sccm for 10 hours to passivate the catalyst. No heating was applied, but the oxygen chemisorption and partial oxidation exotherm caused a momentary temperature rise. After 10 hours, the gas feed was changed to pure air, the flow rate was lowered to 200 sccm and the temperature was raised to 300° C. at a rate of 1° C./minute and then kept at 300° C. for two hours. At this point, the catalyst was cooled to ambient temperature and discharged from the glass tube reactor. It was transferred to a 316-SS tube reactor of 0.51" I.D. and placed in a clam-shell furnace. The catalyst bed was flushed with a downward flow of helium for a period of two hours, after which time the gas feed was switched to pure hydrogen at a flow rate of 500 sccm. The temperature was slowly raised to 120° C. at a temperature interval of 1° C./minute, held there for a period of one hour, then raised to 250° C. at a temperature interval of 1° C./minute and held at that temperature for 10 hours. After this time, the catalyst bed was cooled to 180° C. while remaining under a flow of pure hydrogen gas. All flows were directed downward.

Examples 1-6

Fischer-Tropsch Activity

A catalyst prepared and activated as described above was subjected to a synthesis run in which the catalyst was contacted with hydrogen and carbon monoxide in ratios between 1.2 and 2.0 at temperatures between 205° C. and 235° C., with a total pressure of 5-20 atm and a total gas flow rate of 2100-6000 cubic centimeters of gas (0° C., 1 atm) per gram of catalyst per hour. Results are set forth in Table 2.

It can be seen from the results in Table 2 that the hybrid Fischer-Tropsch catalyst of the present invention prepared using ZSM-12 zeolite is effective for the conversion of synthesis gas to give a liquid hydrocarbon product substantially free of solid wax under commercially viable process conditions. Further, the yield of undesired light gaseous products of $C_1$-$C_4$ is low and the yield of desirable $C_{5+}$ hydrocarbons is above 80%.

TABLE 2

| Example Number | 1 | 2 | 3 | 4 | 5 | 6 |
|---|---|---|---|---|---|---|
| TOS, h | 100 | 190 | 315.0 | 363.0 | 433.0 | 483.0 |
| Yield Time, h | 70.2 | 64.0 | 46.0 | 48.0 | 25.0 | 46.0 |
| Temperature, ° C. | 220.0 | 220.0 | 225.0 | 225.0 | 225.0 | 225.0 |
| 1000/T, ° K⁻¹ | 2.028 | 2.028 | 2.007 | 2.007 | 2.007 | 2.007 |
| Pressure, atm | 10 | 20 | 10 | 10 | 10 | 10 |
| SV, mL/g/h | 1200 | 1200 | 2100 | 2100 | 2100 | 2100 |
| H₂/CO Fresh Feed | 2.00 | 2.00 | 1.80 | 1.80 | 1.80 | 1.80 |
| H₂/CO Inlet to Reactor | 1.38 | 1.37 | 1.31 | 1.33 | 1.8 | 1.41 |
| H₂/CO usage | 2.24 | 2.17 | 2.29 | 2.32 | 2.24 | 2.26 |
| CO/(H₂ + N₂ + CO), % | 26% | 26% | 36% | 36% | 36% | 36% |
| Recycle Ratio | 3 | 3 | 1 | 1 | 0 | 1 |
| Per Pass CO conv | 34.40% | 46.90% | 26.70% | 25.90% | 58.50% | 25.90% |
| H₂ Conv. = | 92.6% | 96.9% | 78.4% | 76.6% | 74.5% | 72.5% |

TABLE 2-continued

| Example Number | 1 | 2 | 3 | 4 | 5 | 6 |
|---|---|---|---|---|---|---|
| CO Conv. = | 83.9% | 90.6% | 60.2% | 58.2% | 58.5% | 56.6% |
| Rate, sccm CO/g/h | 266 | 287 | 455 | 440 | 442 | 428 |
| Ln(Rate) | 5.58 | 5.66 | 6.12 | 6.09 | 6.09 | 6.06 |
| Rate, g $CH_2$/g/h | 0.17 | 0.18 | 0.28 | 0.27 | 0.28 | 0.27 |
| Rate, mL $C_5^+$/g/h | 0.17 | 0.20 | 0.30 | 0.28 | 0.28 | 0.28 |
| % $CO_2$ | 1.30% | 1.30% | 0.70% | 0.80% | 1.00% | 0.70% |
| % $CH_4$ | 10.7% | 8.2% | 10.5% | 11.4% | 12.0% | 11.1% |
| % $C_2$ | 1.5% | 1.0% | 1.2% | 1.2% | 1.3% | 1.2% |
| % $C_3 + C_4$ | 9.8% | 6.0% | 9.0% | 9.7% | 10.2% | 9.4% |
| % $C_5+$ | 76.7% | 83.5% | 78.5% | 76.9% | 75.4% | 77.6% |
| % $C21+$ | 0% | 0.3% | 0.8% | 0.6% | 0.7% | 0.4% |
| $C_2^=/C_2$ | 0.6% | 0.0% | 2.9% | 2.9% | 4.4% | 3.4% |
| $C_3^=/C_3$ | 20.6% | 21.8% | 45.4% | 45.6% | 57.3% | 46.4% |
| $C_4^=/C_4$ | 47.4% | 50.1% | 70.2% | 69.6% | 73.7% | 70.8% |
| Degree of branching | 15.4% | 13.5% | 11.7% | 11.3% | 12.0% | 12.1% |
| Solid wax, g | 0 | 0 | 0 | 0 | 0 | 0 |

Comparative Example

Comparison of Hybrid Catalyst Prepared with ZSM-12 and Hybrid Catalyst Prepared with ZSM-5

A catalyst comprising 7.5% weight Co/0.19% weight Ru on 72% weight ZSM-5 and 0.18% weight alumina was prepared and activated according to the following procedure. First, ruthenium nitrosyl nitrate was dissolved in water. Second, cobalt nitrate was dissolved in acetone. The two solutions were mixed together and then added to 1/16" extrudates of alumina (20 weight % alumina) bound ZSM-5 zeolite (Zeolyst CBV 014, Si/Al=40). After the mixture was stirred for 1 hour at ambient temperature, the solvent was eliminated by rotavaporation. Then the catalyst was dried in an oven at 120° C. overnight and finally calcined at 300° C. for 2 hours in a muffle furnace.

The catalyst was subjected to a synthesis run in which 20 grams of the catalyst was contacted with a hydrogen and carbon monoxide ratio of 1.6 at a temperature of 220° C. with a total pressure of 10 atm and a total gas flow rate of 2028 cubic centimeters of gas per gram catalyst per hour. The data presented in Tables 3 (without recycle) and 4 (with recycle) provide a comparison of hybrid, integral catalysts prepared with ZSM-5 and ZSM-12 zeolites.

TABLE 3

| | Hybrid catalyst prepared with ZSM-12 | Hybrid catalyst prepared with ZSM-5 |
|---|---|---|
| TOS, h | 338 | 343 |
| Run Conditions | | |
| Temp, ° C. | 220 | 220 |
| Pres, atm | 10 | 10 |
| Reactant SV, mL/g/h | 1200 | 1200 |
| Recycle Ratio | 0 | 0 |
| Results | | |
| CO Conv, % | 24.20% | 42.10% |
| $H_2$ Conv, % | 29.60% | 53.70% |
| Total Conv, % | 27.50% | 49.30% |
| Rate, g $CH_2$/g/h | 0.122 | 0.151 |
| Rate, mL $C_{5+}$/g/h | 0.134 | 0.153 |
| $CH_4$ select, % | 9.90% | 12.20% |
| $C_2$, select % | 1.10% | 1.70% |
| $C_3$-$C_4$, select % | 6.50% | 9.40% |
| $C_{5+}$, select, % | 82.20% | 75.80% |
| $C_{21+}$, select, % | 4.58% | 4.00% |

TABLE 3-continued

| | Hybrid catalyst prepared with ZSM-12 | Hybrid catalyst prepared with ZSM-5 |
|---|---|---|
| $CO_2$ select, % | 0.40% | 0.90% |
| Solid wax, g | 0 | 0 |

TABLE 4

| | Hybrid catalyst prepared with ZSM-12 | Hybrid catalyst prepared with ZSM-5 |
|---|---|---|
| TOS, h | 749 | 652 |
| Run Conditions | | |
| Temp, ° C. | 225 | 225 |
| Pres, atm | 15 | 15 |
| Reactant SV, mL/g/h | 450 | 450 |
| $H_2$/CO Fresh Feed | 2 | 2 |
| $H_2$/CO Inlet to Reactor | 1.21 | 1.6 |
| $H_2$/CO usage | 2.29 | 2.08 |
| Results | | |
| Per Pass CO Conv, % | 46.8% | 59.3% |
| $H_2$ Conv, % | 97.7% | 96.0% |
| CO Conv, % | 83.1% | 91.2% |
| Rate, g $CH_2$/g/h | 0.058 | 0.068 |
| Rate, mL $C_{5+}$/g/h | 0.062 | 0.062 |
| $CH_4$ select, % | 9.3% | 17.5% |
| $C_2$, select % | 1.4% | 2.3% |
| $C_3$-$C_4$, select % | 9.1% | 8.3% |
| $C_{5+}$, select, % | 79.6% | 69.1% |
| $C_{21+}$, select, % | 0.5% | 0.1% |
| $CO_2$ select, % | 0.7% | 2.8% |
| Solid wax, g | 0 | 0 |

It can be seen from Tables 3 and 4 that a hybrid, integral catalyst prepared with ZSM-12 surprisingly results in a higher yield of desired $C_{5+}$ product while producing lower yields of undesired light gases with good conversion of synthesis gas. No solid wax was seen for either catalyst under these reaction conditions. It is apparent from observation that the product contains less than about 5 weight % $C_{21+}$ normal paraffins.

While various embodiments have been described, it is to be understood that variations and modifications may be resorted to as will be apparent to those skilled in the art. Such variations and modifications are to be considered within the purview and scope of the claims appended hereto.

What is claimed is:

1. A method of performing a synthesis gas conversion reaction, the method comprising contacting a hybrid Fischer-Tropsch catalyst comprising a ZSM-12 zeolite extrudate impregnated with cobalt with synthesis gas, the synthesis gas comprising hydrogen and carbon monoxide at a ratio of hydrogen to carbon monoxide of between about 1 and about 3, at a temperature of between about 180 and about 280° C. at a pressure of about 5 and about 30 atmospheres to yield a hydrocarbon product containing:

less than about 10 weight % methane;
greater than about 75 weight % $C_{5+}$;
less than about 15 weight % $C_2$-$C_4$; and
less than about 5 weight % $C_{21+}$.

2. The method of claim 1, wherein the product contains:
between about 3 and about 10 weight % $CH_4$; and
between about 3 and about 10 weight % $C_2$-$C_4$.

3. The method of claim 1 wherein the product contains less than about 5 weight % $C_{21}+$ normal paraffins.

4. The method of claim 1 wherein the synthesis gas comprises hydrogen and carbon monoxide at a ratio of hydrogen to carbon monoxide of between about 1.5 and about 2.

5. The method of claim 1 wherein the conversion reaction occurs at a temperature of between about 220 and about 235° C.

6. The method of claim 1 wherein the conversion reaction occurs at a pressure of between about 20 and about 30 atmospheres.

* * * * *